United States Patent [19]

Gonser

[11] Patent Number: 4,516,195
[45] Date of Patent: May 7, 1985

[54] MULTI-FUNCTION DENTAL OPERATING LIGHT SOURCE

[75] Inventor: Donald I. Gonser, York, Pa.

[73] Assignee: Dentsply Research & Development Corp., Milford, Del.

[21] Appl. No.: 566,235

[22] Filed: Dec. 28, 1983

[51] Int. Cl.³ .............................................. F21V 9/08
[52] U.S. Cl. ..................................... 362/281; 362/33; 362/804; 362/293; 362/323
[58] Field of Search .................. 362/293, 804, 33, 281, 362/323

[56] References Cited

U.S. PATENT DOCUMENTS

| | | | |
|---|---|---|---|
| 2,606,477 | 8/1952 | Leslie et al. | 88/16.4 |
| 2,699,536 | 1/1955 | Roth et al. | 340/49 |
| 3,179,791 | 4/1965 | Mole | 240/10.1 |
| 3,202,811 | 8/1965 | Hall, Jr. | 240/1.1 |
| 3,832,539 | 8/1974 | Oram | 362/293 |
| 3,842,254 | 10/1974 | Dianetti | 362/293 X |
| 4,009,382 | 2/1977 | Nath | 362/32 |
| 4,196,460 | 4/1980 | Schreckendgust | 362/804 X |
| 4,385,344 | 5/1983 | Gonser | 362/32 |
| 4,400,765 | 8/1983 | Kochem | 362/804 X |
| 4,450,139 | 5/1984 | Bussiere et al. | 362/804 X |

FOREIGN PATENT DOCUMENTS

2604921 9/1976 Fed. Rep. of Germany ...... 362/804

Primary Examiner—Peter A. Nelson
Attorney, Agent, or Firm—C. Hercus Just; Edward J. Hanson, Jr.

[57] ABSTRACT

A multi-function dental operating light source comprises a series of optical filters and flat reflectors mounted upon a turntable at spaced locations around the periphery, the turntable being rotatable about a fixed axis relative to a stationary tungsten halogen lamp having a parabolic reflector and including stationary spherical mirrors mounted to reflect light forward. The optical filters are adapted respectively to produce pure white light beams free of any color hue for oral illumination purposes, shade-matching light beams, no-cure light beams to prevent polymerization of light-curable resins when exposed to said light for observation purposes, a photocuring light beam extending through a light-condensing cone and suitable to effect polymerization of light curable resins, and means to adjust the voltage supply to the lamp filament to produce by the respective optical filters, mirrors, and light-condensing cone the desired type of illumination and photocuring functions the optical filters respectively are capable of producing.

25 Claims, 14 Drawing Figures

MULTI-FUNCTION DENTAL OPERATING LIGHT SOURCE

BACKGROUND OF THE INVENTION

In modern dental practice, different types of illumination and photocuring functions are required and, at present, these, in general, are supplied respectively by individual different lamps packaged as separate light sources, thus requiring a number of individual pieces of equipment for use in a dental operatory. Also, at present, high rents necessitate maintaining operatory rooms in relatively small economical sizes, whereby the smaller, simpler, and less space-consuming equipment is, the better it can be accommodated comfortably in present day operatories. The present invention is directed to such minimizing of required illumination equipment as well as rendering the same more efficient and of improved quality.

For many years, it has been customary for dentists to select operatories facing north wherever possible in order to obtain natural daylight as close as possible to pure white light, i.e., the absence of color hue. Such efforts are frustrated on cloudy or rainy days and the time of the year, however, whereby one has to resort to using artificial light from lamp sources upon which attempts have been made to modify the same to at least approach pure white light at an acceptable color temperature such as 5500° K., for example.

Dentistry presently requires illumination of as nearly as possible pure white light to be directed at dental targets for viewing the same such as the interior of an oral cavity; similar somewhat intensified white light illumination suitable for shade matching of artificial teeth with natural teeth; photocure light power of a type to effect curing of light-curable resins or plastics used for dental restorations of various kinds and similar purposes; and illumination of dental targets of a type which permits viewing the same without effecting premature polymerization of visible light-curable resins or plastics, such as those used for dental restorations of various kinds and especially while forming and shaping fillings and similar restorations of plastic material prior to curing the same. As indicated above, lights or lamps to produce standard illumination now are available only as an individual units. As far as is known, a no-cure type of illumination is not available to date.

In the prior art of lighting and illumination in general, attempts have been made to utilize a single light source to produce, for example, different colors for entertainment and stage use. Typical examples of this type of illumination are illustrated in prior U.S. Pat. Nos. 2,606,477 to Leslie et al, dated Aug. 12, 1952 and 3,179,791 to Mole, dated Apr. 20, 1965. As a slight modification of the principles illustrated in the foregoing patents, prior U.S. Pat. No. 2,699,536 to Roth et al, dated Jan. 11, 1955 discloses a headlamp arrangement on certain vehicles for signaling purposes and in which the light source remains fixed and movable lenses cause the projections of a spiral pattern of beams.

There also has been prior activity in reflecting beams from a light source in a manner to intensify beams therefrom by reflection to and from curved reflectors for ultimate direction through an output window or lens, one example being the subject matter of prior U.S. Pat. No. 3,202,811 to Hall, Jr., dated Aug. 24, 1965.

Unlike the operation and construction of these cited prior art patents, the present invention utilizes a single lamp as a light source and by means of a series of light modifying optical filters and related elements, coupled with variable control of voltage to the filament of the light source, at least most if not all of the various types of dental applications for illumination and photocuring set forth above can be produced by relatively simple structures of a compact nature, details of which are set forth below.

The present invention is the result of expanding and increasing the versatility and convenience of the inventions in applicant's prior U.S. Pat. No. 4,385,344, dated May 24, 1983, and his pending U.S. application Ser. No. 492,286, filed May 6, 1983.

SUMMARY OF THE INVENTION

Among basic objects of the present invention, it is a major objective to provide a multi-function dental operatory light source in which, by simple rotation of a turntable on which a limited number of light beam modifiers of a single stationary light source are mounted for selective positioning relative to said light source and manual setting of a potentiometer and the electronic control circuitry therefor to vary the voltage to the filament of the light source as required for each modifier, whereby at least the most commonly required dental illumination needs and photocuring function are supplied by a single instrument.

Ancillary to the foregoing object, it is a further object to have said single instrument selectively supply substantially pure white light to view dental targets, intensify said white light at a higher color temperature a limited amount for shade matching purposes simply by varying the aforementioned voltage to the lamp filament by adjusting said potentiometer, supply non-polymerizing light illumination for viewing dental materials which otherwise would light polymerize light-sensitive materials, and supplying polymerizing light capable of quickly polymerizing light-polymerizable resins and plastics when required, whereby simple rotation of the aforementioned turntable on which said several light-modifying optical devices are supported in spaced relationship produces the desired types of dental illumination and photocure function from a single light source.

Another object of the invention is to provide a heat-absorbing filter positioned adjacent and in the path of the light beam emanating from the parabolic reflector, whereby the light beam is intercepted by the heat absorbing filter and produces relatively cool light, of reduced infrared wavelengths, and less thermal stress is placed upon the modifying optical filters when positioned in the light beam and in front of the reflector of the lamp.

A further object of the invention is to provide as a light source a tungsten halogen lamp having a parabolic reflector to produce parallel light rays, and further to provide one or more light filters selectively positionable in the light path from the lamp and the reflector therefor. Beam-splitting flat mirrors also are positioned in the standard illumination beam and the no-cure beam which split the light beam into two separate light beams transmitted through said optical filters and reflect the same in separate directions respectively to spherical reflectors positioned at opposite sides of said lamp. Since each of the split beams are spaced apart, they reflect each of the beams forward, toward and through a fixed transparent window spaced forward from said lamp. Each of the separate light beams reflected from said spherical reflectors cross each other at a specified distance from said reflectors and are blended with the other beams to provide an illumination area of limited widths and height at a location spaced forward from said window. The crossover of said light beams is at a range of distances at which a dentist normally positions an illuminating light source from a dental target such as an oral cavity. One reason for dual converging light beams is that, when a dentist is manipulating, it is possible to block one light beam with an arm, shoulder, hand, or head, whereby one light beam is left unblocked for illumination purposes.

Still another object of the invention is to provide a base movably mounted relative to a dental chair in an operatory for desired positioning of said base relative to a patient in said chair, and said aforementioned turntable upon which said aforementioned beam-modifying optical filters are mounted and is rotatably supported upon said base for movement around an axis vertical to said base, and further providing releasable position-maintaining means between said turntable and base to firmly hold a selected beam-modifying optical filter and associated beam-splitting flat reflectors in operable position adjacent said aforementioned lamp.

A further object ancillary to the immediate foregoing object is to mount said lamp fixedly and centrally adjacent one side edge of the base, which preferably is a plate, and also fixedly position said aforementioned spherical reflectors adjacent said same side edge of said base plate and spaced from opposite sides of said lamp, and said aforementioned transparent window is fixed to the opposite side edge of said base plate.

One further object of the invention is to enclose all of the elements set forth above in a housing fixed to said base plate and said base plate and housing being pivotally supported relative to one end of a movably mounted arm, and manipulating handles being mounted upon said housing to facilitate positioning said base plate and housing as desired relative to a dental target.

One other object of the invention is to provide a potentiometer in an electronic circuit to said aforementioned lamp which is operable selectively to vary voltage to the filament of said lamp as required to effect the functions of the various beam-modifying optical filters to operate in different wavelength ranges in nanometers, the potentiometer having a single manually operable knob which, in addition to the manual means by which the turntable is rotated, is the only other means requiring manual operation to effect the respective functions of the beam-modifying optical filters and the resin curing unit on the turntable.

Still another object of the invention is to utilize optical filters and related mechanisms to change illumination emanating from a light source such as, for example, a tungsten halogen lamp which produces various desired Kelvin ranges respectively arranged to produce: white illumination between 4700° K. and 5100° K. for normal observation of dental targets; intensify the blue, green, and red toward the blue and thereby increase the lumens for shade matching to about 5500° K. or in a range between 5400° K. and 5900° K.; reduce the color temperature to less than 1667° K. and use the same with a filter which eliminates the blue range of the spectrum between 400 and 500 nm, and permits wavelength greater than 500 nm to pass through the optical filter, which renders polymerizing of visible light-polymerizable resins and plastics unaffected by the light. However, beams between 500 and 715 nm are not obstructed for viewing purposes and allow sufficient illumination to place and architecture restorative dental materials.

Details of the foregoing objects and of the invention as well as other objects thereof, are set forth in the following specification and illustrated in the accompanying drawings-comprising a part thereof.

DETAILED DESCRIPTION OF THE PREFERRED EMBODIMENT OF THE INVENTION

It is believed desirable to set forth herein certain definitions and criteria pertinent to the present invention as follows:

Photometric power is that which the eye sees expressed in lumens/square meter or lumens/square foot.

Radiometric power is actual power from a given source expressed in watts/cm².

Nanometer (nm) is a unit of length of one cycle equal to one billionth of a meter or $10^{-9}$ meters.

Lumen (Lm) is a unit of luminous flux.

Footcandle (fc) is a unit of illuminance equal to one lumen per square foot.

Lux (Lx) is a unit of illuminance equal to one lumen per square meter.

Kelvin (K) is a unit of temperature equal in magnitude to 1° C. but based on an absolute temperature scale in which 0° K.=−273.15° C.

Wavelength is the distance between two successive points of a periodic wave in the direction of propogation of a beam of light.

Hue is the attribute of a light source or object that determines whether it is perceived as red, orange, yellow, green, blue, or violet, without regard to the other aspects such as saturation and brightness.

In accordance with the present invention, the light source preferably is generated by electric current connected to a tungsten halogen lamp having a parabolic reflector, but other lamp types may be used such as various arc-type lamps which produce an acceptable optical spectrum. One particular selected tungsten halogen lamp found to be highly successful can be operated as high as 3400° K., but this is only exemplary and not restrictive. With this as a benchmark, however, for purposes of illustrating at least one example of the invention, the various lights or illuminations designed to be produced by such lamp require the use of specific optical filters to achieve the objectives of the invention for different dental illuminations and for photocuring purposes. In order to effect relatively cool light beam operation of the multi-function illuminating system of the invention, a heat absorbing filter preferably is positioned immediately in front of the lamp reflector in the light beam. With this exception, all of the other optical filters are interference filters which either pass or reject certain wavelengths of light, as designed and desired. These optical filters comprise layers of certain materials selected for their known index of refraction and are laminated, for example, in a vacuum deposition chamber, and laid on a suitable substrate. Such optical filters shape the spectrum of a light beam passing therethrough to a desired portion or section of the optical spectrum for specific passage or rejection of light beams of various wavelengths.

Light beams also have color temperature units expressed as K or Kelvins. According to one specific set of examples of ranges of color temperatures, but without limitation thereto, relative to the present invention, the optical filter to produce substantially pure white light for normal illumination of dental targets from the reflector of the lamp referred to produces beams having a color temperature between 4700° K. and 5100° K. in the wavelength range between 400 and 715 nm and in which the blue, green, and red wavelength ranges are proportioned to produce pure white light.

For shade matching of artificial teeth with natural teeth, this temperature is increased to approximately 5500° K. but with an adjustable range from 5400° K. to 5900° K. which is accomplished by increasing the voltage beyond the standard illumination range supplied to the filament of the lamp.

For observation of a dental target which requires illumination and, therefore, exposure of light-curable resins or plastics to certain beams without activating the material, a filter to produce a beam having a color temperature of less than 1667° K. is used but the filter is one which eliminates the 400 to 500 nm wavelength range, yet retains light beams between the 500 and 715 nm wavelength range which is necessary for viewing purposes and allows placing and shaping the observed light-sensitive material such as visible light-curable filling or denture base resins or plastics. Such beams are in the yellow-red region of the spectrum.

For curing light-sensitive resins and plastics, the invention includes a photocure heat reflecting band pass filter positionable opposite the parabolic reflector of the lamp, and heat absorbing filter which has a color temperature of less than 1667° K. with its light flux primarily in the 400 to 500 nm wavelength range and rejects beams in which the wavelength range between 500 and 715 nm. A fixedly mounted light-condensing cone is used to which an external supplemental light-condensing cone is attached by the operator when photocuring is required.

In producing the above-described types of illumination and for photocuring purposes, another objective of the invention preferably is to project beams from the apparatus in a columnated form and of reasonable dimensions in area at a conventional distance of approximately in the range of between 24 and 37 inches between the dental target and the light source.

One further object of the invention is to provide comfort and safety means for a patient, especially while the relatively strong photocure energy is directed toward the patient. This is in the form of a switch in the circuit to the light source lamp whereby, when the turntable is rotated to dispose the photocure light cone in the operative position relative to the lamp, said switch automatically is opened to deactivate the lamp while a supplemental external light-condensing cone is positioned manually upon the primary or internal light-condensing cone and during such operation, the light from the lamp cannot project the light into the patient's eyes.

As an improvement ancillary to the foregoing object, the circuit to the lamp also includes an additional, preferably push-button, switch which is actuated easily to restore current to the lamp after the external supplemental cone has been mounted operatively upon the internal primary cone and, still further, a timer of limited time duration also is in the lamp circuit and functions to disconnect current from the lamp after a pre-set time elapses, such as ten seconds duration, for example, thereby automatically limiting exposure by the photocure light beam. The above described push-button switch may be actuated repeatedly, however, to afford as much photocuring as required.

Having set forth above exemplary parameters of physical aspects of the illuminating apparatus of the present invention, it is to be understood that the criteria described may be changed within reasonable limits without departing from the spirit of the invention. One specific illustration of physical apparatus which utilizes said criteria is set forth below.

THE APPARATUS

Figure 1:
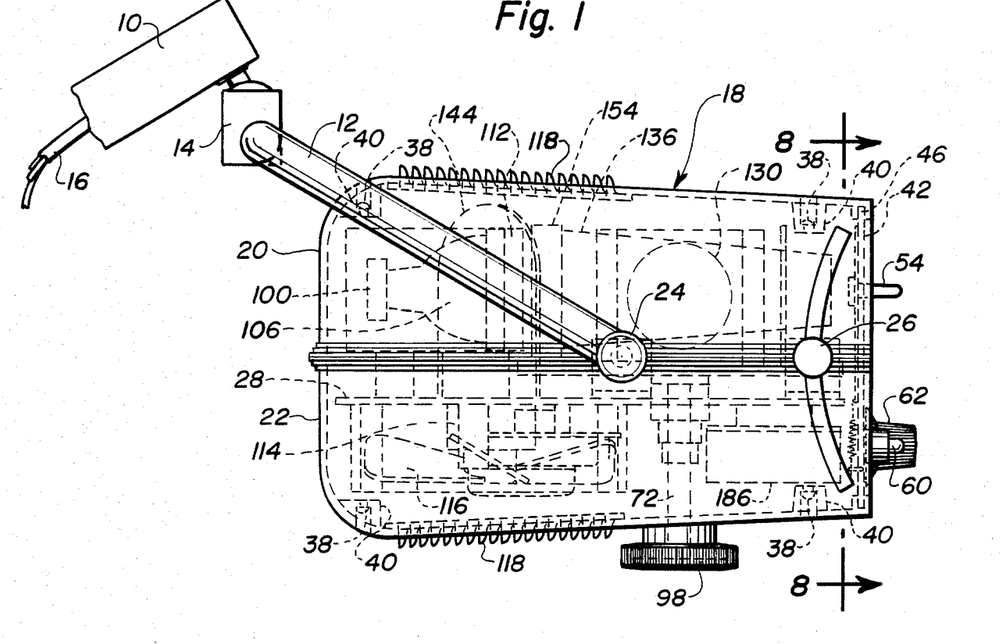
FIG. 1 is a side elevation of a dental operating light embodying the principles of the present invention and shown mounted on a fragmentally illustrated supporting arm.
Figure 2:
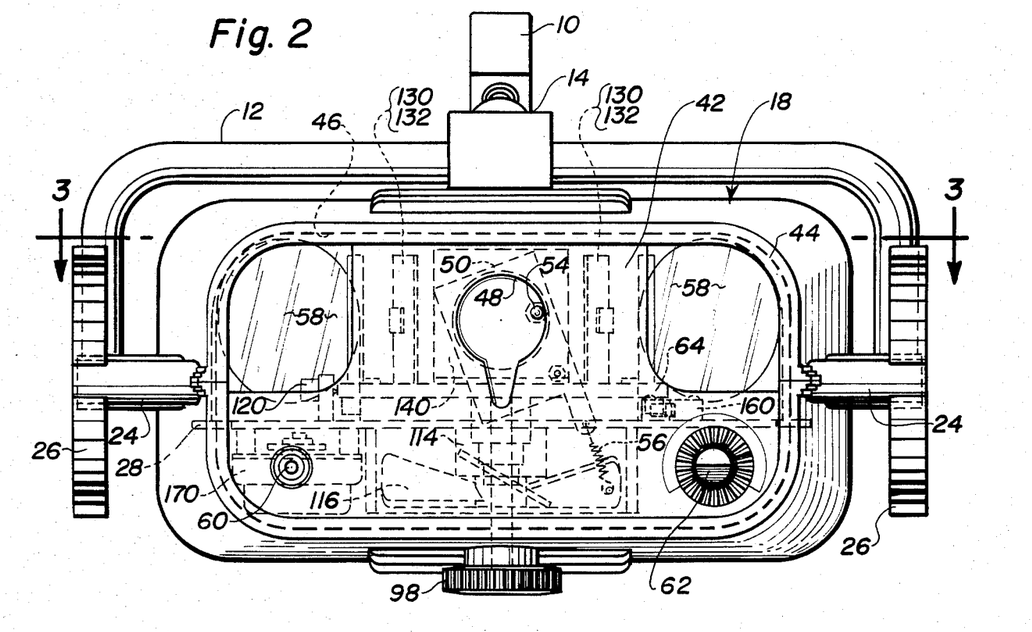
FIG. 2 is a front elevation of the light shown in FIG. 1.
Figure 3:
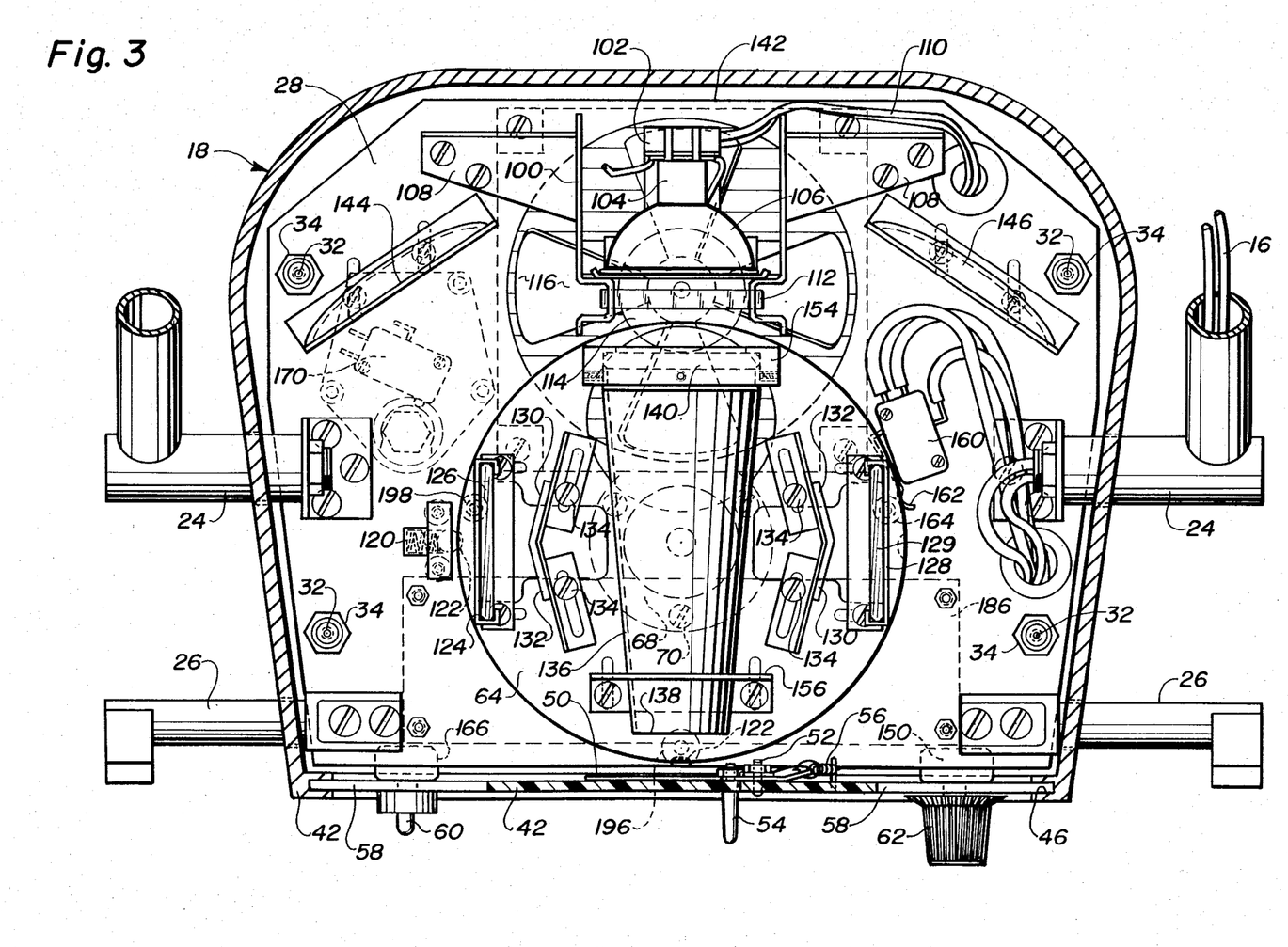
FIG. 3 is a horizontal sectional view of the light shown in FIGS. 1 and 2 taken on the line 3—3 of FIG. 2, said view being on a larger scale than the views in FIGS. 1 and 2.

Referring to FIGS. 1 to 3 of the drawings, it is intended that the multi-function dental operating light source comprising the present invention be supported by the outer end of an appropriate arm 10 which extends either from a wall, ceiling, or post pedestal in an operatory. A U-shape member 12 is connected by a swivel 14 to the outer end of arm 10 and it will be understood that an electrical supply cord is located in conduit 16 and extends from a suitable power line source, not shown, and appropriate electrical thermal breakers, current-limiting switch, and connect-disconnect switch and its wiring are located in said conduit which extends in conventional manner through the arm 10, swivel 14, and U-shape member 12 to the interior of the light head housing 18 which preferably comprises an upper section 20 and a lower section 22 that are detachably connected. Opposite sides of the housing 18 are connected by pivots 24 to the outer ends of member 12.

The sections 20 and 22 of housing 18 preferably are molded from suitable, rigid plastic material for durability as well as to provide electrical insulation properties. Further, a manually-engageable handle 26 extends from each of the opposite sides of the housing 18 for purposes of swivelling the housing to any desired location and position for purposes of directing illumination or photocuring light beams therefrom to a dental target such as an oral cavity or tooth of a patient. It will be understood that the pivots 24 and swivel 14 have sufficient friction to maintain a desirable location and position of the housing 18 after the same has been adjusted to a working position.

Figure 9:
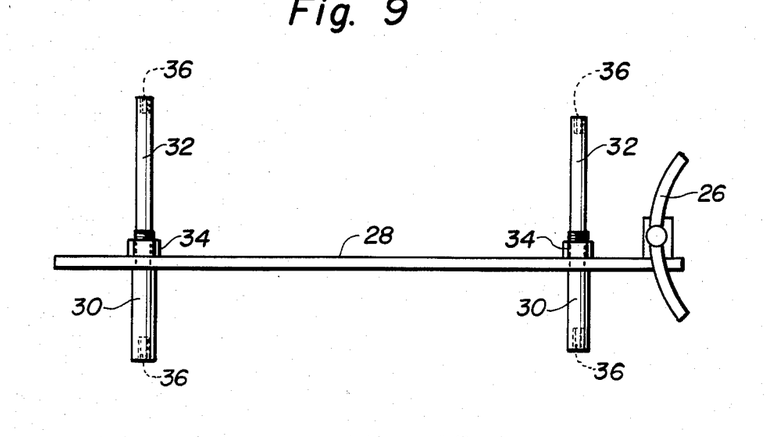
FIG. 9 is a side elevation of details of the base in the housing of the light shown in FIGS. 1 to 3.

Referring particularly to FIG. 3, a description of the contents of the housing 18 is as follows. In said figure, it will be seen that there is a base 28 which preferably is a plate substantially parallel to the meeting lines of sections 20 and 22 of the housing, said base plate preferably being of metal, such as aluminum, and may be anodized black or in color. A plurality of posts 30 extend perpendicularly in opposite directions from the base 28 as shown in FIG. 9 which is substantially a side view of the base plate and shows the posts 30 better than if they would appear in FIG. 1 if shown in phantom. The upper portions 32 of the posts are of a smaller diameter and extend through suitable holes in the base plate. The lower part of the upper portions 32 are threaded to receive clamping nuts 34 and accomplishes this without threading the entire portions 32 by the part thereof which receives the nuts 34 being of a slightly larger diameter than the upper part of said portions. The outer ends of the posts 30 and upper portions 32 have tapped holes 36 extending thereto for purposes of receiving connecting screws 38 which extend through bosses 40 shown in FIG. 1 on the interior of the upper and lower sections 20 and 22 of the housing 18. From FIG. 3, it also will be seen that there are four of the composite posts 30, 36, respectively adjacent the corners of the base 28 and these comprise the means for holding together the upper and lower sections 20 and 22 of the housing 18.

The front wall of the housing 18 has a transparent window panel 42 which, in vertical elevation, is shown in FIG. 2 in the forward portion of the housing 18 and has a bezel 44 surrounding the same. Said bezel has a continuous groove 46 extending thereinto as best seen in FIGS. 2 and 3 and said groove receives the edge portions of the transparent window panel 42 for purposes of securing it in operative position. The panel has a small opening or aperture 48 near the upper portion and midway between the opposite sides through which the photocuring light can pass when the same is open, details of which are described hereinafter. The opening 48, however, normally is closed except when the external light-condensing cone is mounted upon the primary internal cone, whereby its effects are employed to activate light-curable resins and the like when aligned with said opening. Closing of opening 48 is effected by a closure in the form of a pivoted plate 50 which is shown in edge view in FIG. 3 in the lower portion of said figure. The closure 50 is supported upon a pivot bolt 52. To manipulate the closure, a pin 54 which is attached thereto projects through the opening 48 as clearly shown in FIG. 2. It is otherwise shown in FIG. 3, where it will be seen that it is adequate for manual engagement. Closure 50 normally is maintained in closed position in a yieldable manner by means of return spring 56. The window panel 42, in each of the opposite upper corners thereof, is provided with clear transparent window portions 58 and, otherwise, the window panel 42 is opaqued, such as by painting the innersurface thereof or otherwise. The lower opposite corners of the window panel 40 also are provided respectively with holes through which a push-button actuator 60 and a shaft of a potentiometer extend.

Figure 10:
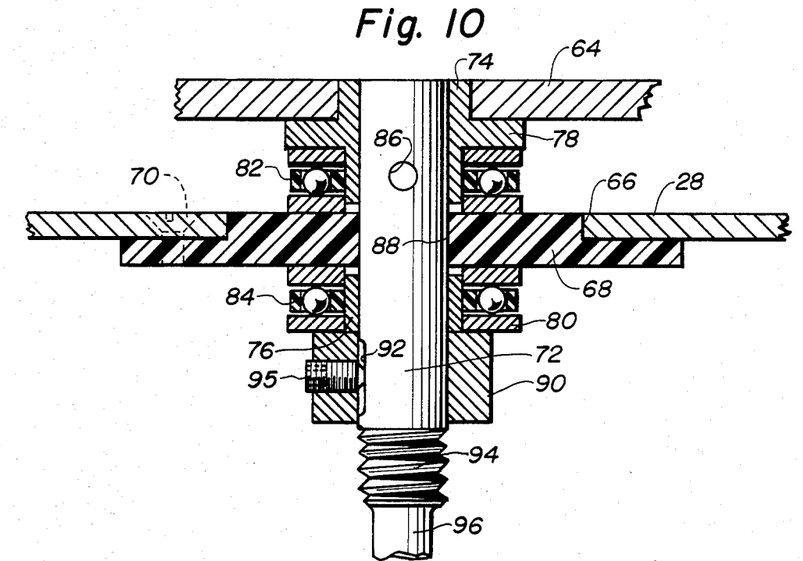
FIG. 10 is a sectional detail of a rotatable assembly within the housing of the light in FIGS. 1 to 3.

Base plate 28 supports a number of elements within housing 18, among the more important of which is a turntable 64 which is shown in plan view in FIG. 3. The manner in which the turntable is supported upon the base 28 is best shown in FIG. 10. Said base is provided with a preferably circular opening 66 into which a shouldered, preferably circular insulating insert member 68 is suitably affixed by spaced screws 70, certain of which are shown in FIGS. 3 and 10. Rotatable shaft 72 extends through a central opening in insulating member 68. Vertically spaced portions of the shaft 72 extend through axially aligned upper bushing member 74 and lower bushing member 76. The upper bushing member 74 has a circular flange 78 intermediately of the ends and lower bushing member 76 has only a lower circular flange 80.

Positioned between the upper face of insulating member 68 and flange 78 is an upper anti-friction bearing 82 and disposed between the lower face of insulating member 68 and flange 80 of the lower bushing member 76 is a lower anti-friction bearing 84. In assembling the arrangement shown in FIG. 10, a transverse pin 86 extends through the lower portions of upper bushing member 74 and shaft 72 and is of such length that it doesn't interfere with the anti-friction bearing 82. The bearing 82 then is mounted upon the upper bushing member 74 and the shaft is extended through hole 88 in insulating member 68. Then the lower anti-friction bearing 84 and lower bushing member 76 are mounted upon the shaft, followed by the mounting of a clamping collar 90 upon the shaft. The lower portion of shaft 72 also has a short flat 92 formed on one side thereof for engagement by a setscrew 95 threaded radially into the clamping collar 90. For purposes of tightening the assembly a nut, not shown, is threaded onto the lower threaded end 94 of shaft 72 and is tightened against the axial assembly, following which setscrew 95 is threaded against the flat 92 to maintain the assembly in operative position, after which the tightening nut, not shown, is removed.

Shaft 72 has a depending portion 96 which extends through the lower section 22 of housing 18 as shown in FIG. 1 and to the projecting end thereof, a manually-engageable, rotatable knob 98 is affixed. The foregoing arrangement is for purposes of positioning the plurality of different beam-developing devices circumferentially mounted upon the turntable 64 relative to a light source, details of which are described hereinafter.

Base 28 is fixedly mounted within the housing 18 by means of the details shown in FIG. 9 and described hereinabove. Also supported fixedly upon said base plate is a lamp housing 100 provided with an insulating base insert 102 which receives and supports base plate 104 of a preferably tungsten halogen lamp 106 which has a parabolic reflector for purposes of producing a columnated light beam. The housing 100 has a pair of ears 108 which are secured by screws to the base 28 as clearly shown in FIG. 3. Connected to insulating base insert 102 are a pair of electric wires 110 which are part of the electric cord 16.

The forward portion of the lamp housing 100 has an opening through which the columnated light beams from the parabolic reflector of lamp 106 are projected and extending across that opening is a heat absorbing filter 112. Further for purposes of rendering operation of the multi-function light source within a dental operatory relatively cool, supported adjacent an opening in the fixed base plate 28 and upon the lower surface thereof is a forced air cooling fan unit 114, shown in phantom in FIGS. 1 and 2 and in plan view in FIG. 3, said unit including a bladed fan 160 which blows ambient room air directly through the housing 100 and in doing so draws air in through louvre 118 in the lower section 22 of the housing and discharges it through louvre 118 in the upper section 20 of housing 18. The electric motor of cooling fan 114 is connected in the circuit shown in FIG. 7, details of which are described hereinafter.

THE TURNTABLE

As described hereinabove in a general manner in the objects of the invention, one of the highly important features of the present invention comprises the turntable 64, the mounting of which is described hereinabove, and of the light beam-modifying elements which are supported thereon for rotation therewith to dispose the same respectively in one of three operative positions relative to the fixed light source 106 which preferably is a tungsten halogen lamp but other lamps of suitable and similar capability to produce a suitable optical spectrum may be substituted therefore, if desired. By actual experience, however, it has been found that said specific type of lamp performs admirably for all of the purposes to which the present invention is directed. Also as indicated above, there are three principal types of light beams capable of being produced by the invention by means of certain individual filters respectively producing (1) pure white illumination meaning the absence of color hue, (2) no-cure illumination, and (3) photocuring power.

With reference to FIG. 3, it will be seen that the base 28 supports a spring-actuated positioning unit 120 which releasably engages complimentary shallow recesses 122 in the periphery of the turntable 64 to accurately position the various beam-modifying optical elements. The first beam-modifying optical element or system comprises a perpendicular frame 124 which supports a perpendicular filter 126 adapted to develop from lamp 106 and adjacent reflectors a standard illuminating beam which is pure white and devoid of color hue. Opposite the frame 124 is a similar perpendicular frame 128 which supports a no-cure filter 129. The light beams from filters 126 and 129, when they individually are disposed adjacent the lamp 106 and in axial alignment thereof respectively are divided by angularly positioned reflecting flat mirrors or light beam-dividers 130 and 132 which are secured by means of a bracket through which screws 134 project for securing the brackets to the turntable 64. One set of such reflecting mirrors 130 and 132 are provided respectively for each of the filters 126 and 129.

Mounted between the sets of reflecting mirrors or members 130 and 132 is a diametrically extending light reflecting device comprising a frusto-conical light-condensing cone member 136. The light output end 138 of member 136 is smaller than the operative light input end which is shown in FIG. 3 to be adjacent the lamp 106 for purposes of receiving columnated light rays from the parabolic reflector of lamp 106 which, after passing through heat absorbing filter 112 said beams pass through a heat reflecting and band pass filter 140 for purposes of reshaping the optical spectrum of the light-curing beam.

STANDARD ILLUMINATION BEAM

Figure 4:
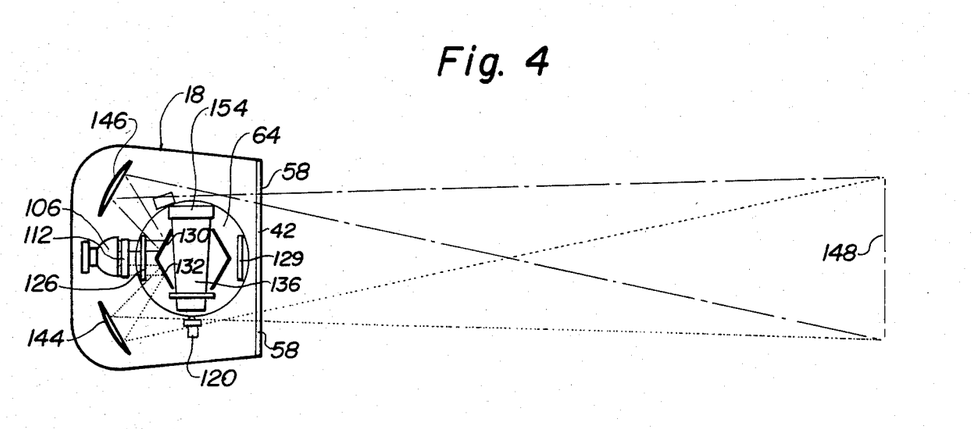
FIGS. 4 to 6 respectively are partially diagrammatic plan views respectively of the three principal operative positions in which the light functions to produce a variety of illuminations for dental use.

Referring to FIG. 4, it will be seen that the filter 126 is disposed adjacent the heat absorbing filter 112 and in immediate alignment with the parabolic reflector of tungsten halogen lamp 106. Adjacent the rear edge of the base, somewhat at the corners thereof, are a pair of spherical reflectors 144 and 146 which are shown better in FIG. 3. These have been adjusted to receive light from the divided beams from the flat mirrors 130 and 132 which, in turn, reflect the light forward through the clear transparent window portions 58 of the front panel 42. Light rays reflected from the spherical reflectors 144 and 146 will travel nearly parallel to each other and spaced apart as shown in FIG. 4 while others will cross each other at defined distances as also shown in said figure, the result being that a column of light beams for standard illumination, comprising pure white light, are developed over a reasonable area 148 which, at a distance of about between 24 and 37 inches from a dental target will be in the range of approximately 4 inches high and 8 inches wide, but such description primarily being exemplary rather than restrictive.

The beams produced will be of a pure white nature, free of color hue due to the nature of a filter 126. Further by way of a specific example, assume that the color temperature of the lamp 106 is approximately 3000° K. The filter 126 has a color temperature within the range 4700° K. and 5100° K., the wave length range being between 400 nm and 715 nm. The same type of white light also is preferable for shade matching of artificial teeth relative to natural teeth or any other objects requiring color comparison but preferably such light must be of a higher color temperature such as of the order of 5500° K. This is produced also by optical filter 126 but the voltage to lamp 106 is increased by manipulating the knob 62 connected to potentiometer 150, see FIGS. 3 and 7.

NO-CURE ILLUMINATION

Figure 5:
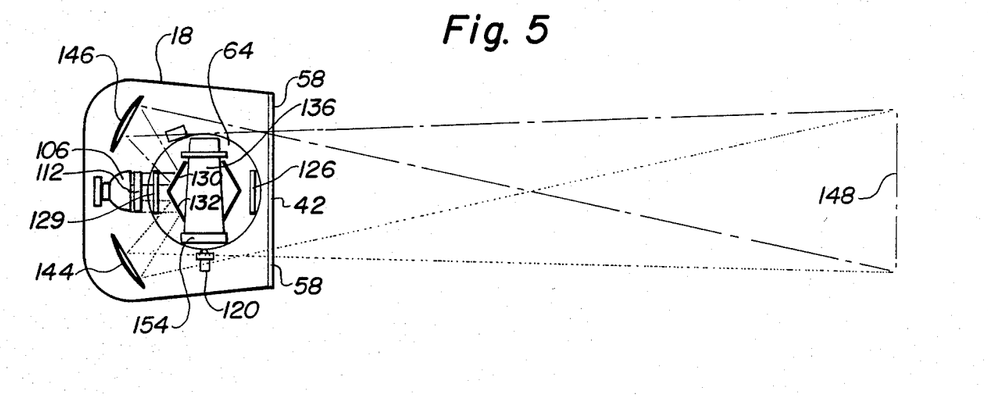

Referring to FIG. 5, the illustration pertains to the no-cure illumination light beam and to produce this, the turntable 64 is rotated to position optical filter 129 opposite the lamp 106, where it will be held by means of one of the depressions 122 in the turntable engaging the spring-pressed ball detent of the positioning unit 120. Optical filter 129 is different from optical filter 126 in that it is designed to reject beams having wavelengths between 400 and 500 nm and therefor are not present in the light beam produced of the lamp whereby the resulting non-curing light beams are in the blue region of the visible spectrum and are incapable of polymerizing light-polymerizable plastic. However, the optical filter also is capable of passing the light beams between 500 and 715 nm for purposes of viewing light-curable material, without activating it, such as when the same is being placed, contoured, and characterized in a tooth or teeth. The passage of light beams between 500 and 715 nm is suitable for such illumination and viewing purposes and is in the yellow-red region of the visible spectrum.

As is in regard to the description relative to FIG. 4, the light beams produced by the parabolic reflector of lamp 106 and filter 129 are reflected by the spherical reflectors 144 and 146 to project forward both the parallel light beams and those which cross at defined distances and ultimately result in producing an illuminating area 148 within the ranges stated with respect to optical filter 126 in FIG. 4.

PHOTOCURING LIGHT POWER

Figure 6:
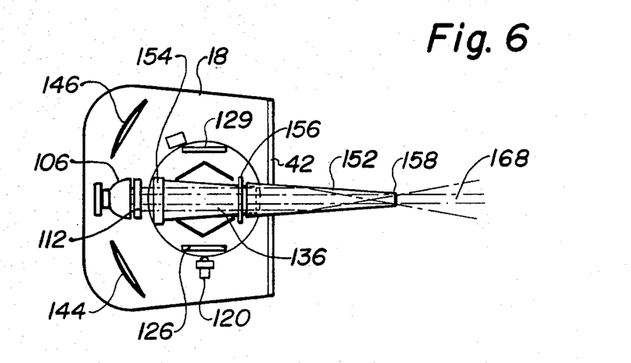
Figure 11:
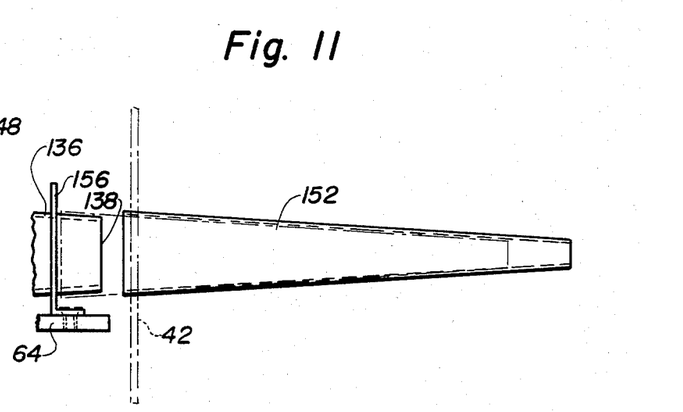
FIG. 11 is a fragmentary side elevation of the supplemental columnating cone of the invention shown in full lines in separated position from the primary cone and the connected position being shown in phantom.

When photocuring function is to be produced by the invention, the turntable 64 is rotated to the position shown in FIGS. 3 and 6 in which the internal primary condensing cone member 136 is disposed with the larger light input end adjacent the lamp 106 and the outer smaller light output end 138 thereof, immediately adjacent the opening 48 in the window panel 42. The light-condensing primary cone member 136 normally is not operated in the condition thereof shown in FIG. 3 but preferably must have a supplemental externally mounted light-condensing cone member 152, shown in FIG. 11, and the larger end thereof is mounted by friction or otherwise upon the small outer end 138 of member 136, as also shown in FIG. 11. Referring to FIG. 3, support 154 is fixed at its lower end to turntable 64 and, in addition to supporting the heat reflecting and band pass filter 140, also supports the larger inner end of the primary light-condensing cone member 136, while the smaller end 138 thereof is supported by a bracket 156 and is attached by screws to turntable 164 as clearly shown in the lower portion of FIG. 3.

Preferably, the interior of light-condensing cone member 136 has a highly specular light-reflective surface which, for convenience, for example, may comprise a highly polished electrobrightened aluminum interior liner, and similarly, such liner lines the inner wall of the supplemental external light-condensing cone member 152 which, when rendered operative, is extended through the small opening 48 in the window panel 42 and then is mounted upon the small end 138 of internal light-condensing cone member 136. A substantial amount of columnation of light rays from the reflector of lamp 106 occurs when mounted as shown by phantom lines illustrated in FIG. 6 by the beams delivered from the discharge end of supplemental external light-condensing cone member 152 which diverge only to a limited extent of about ±10° from the optical axis in order to provide greater penetration of a light-curing beam into light-polymerizable or photocurable plastic material. A low light ray divergence angle is desirable for purposes of activating the same and thereby produce a rigid dental restoration having a greater depth of cure. In normal operation, the tip or outer end 158 is disposed relatively close to the dental target which is to be activated by the light energy emanating therefrom.

When the turntable is disposed in the position shown in FIGS. 3 and 6, wherein the member 136 is in active position for receiving beams from the lamp 106 and assuming that the member 136 is directed toward a patients face such, for example, as when it is positioned for purposes of having the supplemental member 152 affixed thereto, the intense light emanating from the internal primary light-condensing cone member 136 is very bright and would present a safety problem as well as being very annoying to a patient if directed thereto. To prevent this from occurring, the invention contemplates the use of a disconnecting switch 160, best shown in FIGS. 3 and 7, which has an actuating finger 162 engaged by a camming roller 164 which is shown adjacent the finger 162 in FIG. 3. It will be seen that when the turntable 64 is rotated, for example, from either of the positions shown in FIGS. 4 and 5, to the position shown in FIG. 6, the finger 162 will be engaged by the roller 164 and open the switch and thereby disconnect the lamp 106 from the supply circuit so that it will not shine through the open end 138 of member 136.

Figure 7:
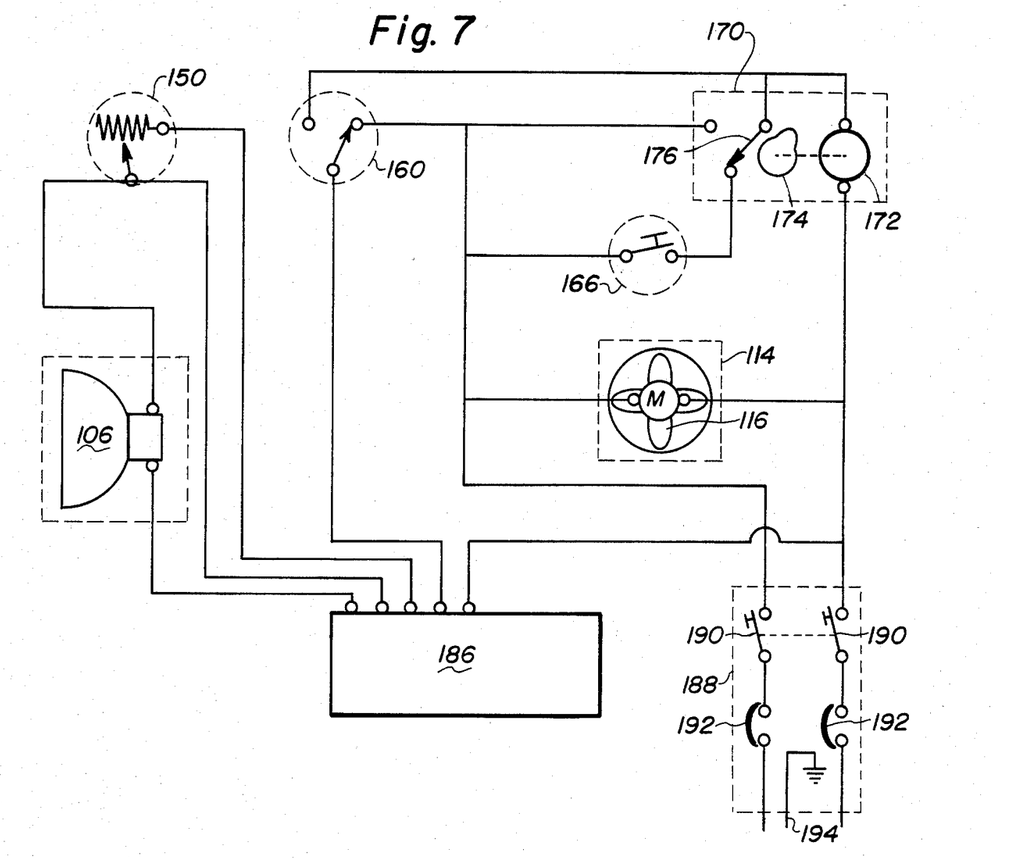
FIG. 7 is a wiring diagram of the circuitry for the light by which illumination is produced and controlled.
Figure 8:
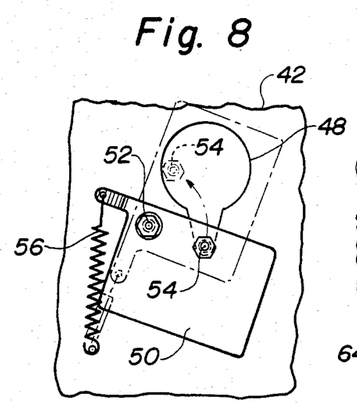
FIG. 8 is a fragmentary view of the closure for the light-curing aperture in the front window of the housing, the open position being shown in full lines and the closed position being shown in phantom.

After the supplemental external light-condensing cone member 152 has been attached over the outer end of member 136, as shown in FIG. 6, an additional switch 166, as seen in FIG. 3 in the lower left-hand corner, is actuated by push-button 60 to re-establish the current to the lamp 106 and also actuate timer motor 172 for the purpose of creating light beams 168 which are of a light-curing nature and emanate from the light output end 158 of the external light-condensing cone member 152. The switch 166 is also shown in FIG. 7 in the circuit diagram. The foregoing arrangement is for safety purposes as well as providing comfort to a patient.

For purposes of limiting the exposure of light beams to tissues, the present invention also contemplates the use of a timer 170, shown diagrammatically in FIG. 7 as a synchronous motor 172 which operates a rotatable cam 174 that is engageable with the switch arm 176 of the timer 170. The timer 170 also is shown in phantom in FIG. 3 adjacent the spherical reflector 134 and said timer is of the type that preferably is set for a fixed period of operation, such as ten seconds or any other fixed period which might be considered the preferred period of a so called "dose" time to assure safety and efficacy of the product. If at the end of such fixed period, additional curing is desired, it is only necessary to press again the push-button 60 of switch 166.

Figure 12:
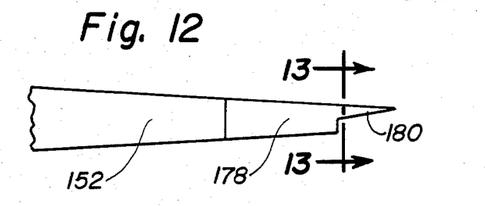
FIG. 12 is a fragmentary modified side view of the cone shown in FIG. 11.
Figure 13:
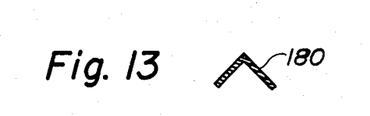
FIG. 13 is a sectional view on line 13—13 of FIG. 12.
Figure 14:
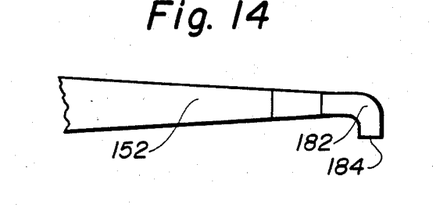
FIG. 14 is a fragmentary side view of a further modification of the cone shown in FIG. 11.

With reference to FIGS. 6 and 11 and especially FIG. 6, wherein diverging beams 168 are illustrated, it is possible to effect further types of light delivery means of the light beams. For example, in FIG. 12, there is illustrated a highly reflective sleeve 178 which connects to or fits over the small end of the external light-reflective cone member 152 and terminates in a forwardly extending reflective point 180 which is shown in cross-section in FIG. 13, as seen on the line 13—13 in FIG. 12. Such an arrangement under certain circumstances give a type of concentration and direction of the beam which is found desirable for certain types of photocuring of light-curable material in locations of difficult access within an oral cavity, such as posterior teeth. Further, by reference to FIG. 14, it will be seen that the outer end of member 15 as provided with a quartz, plastic, or fiber-optic light "tube" 182, which preferably is solid or may be in the form of fibers and has one end fitting into the outer end of external cone member 152 and beams therefrom are directed from the light output end 184 of the light "tube" 182 and it is especially useful for light-curing material within an oral cavity for example, such as a light-activated filling or coating material located in the posterior region of an oral cavity.

The printed circuit shown in FIG. 7 also includes a printed circuit board 186, details of which are not illustrated but it contains electronic elements which are connected by a circuit for a number of different purposes such as regulating the voltage to the lamp 106, providing a soft start for the flow of current to the lamp 106, such as of the order of a few seconds, to provide long life for the lamp; maintaining the voltage constant to the filament of the lamp regardless of power line fluctuations, also maintaining the light output from the lamp constant, not only for all power line voltage fluctuations described above but especially for photocuring, as when light-condensing cone members 136 and 152 are receiving light rays from the reflector of lamp 106 for delivery of the same to the target. The contents of the printed circuit board also replace expensive and heavy, bulky transformers.

In addition, the circuits shown in FIG. 7 include a master switch 188 which is manually operated such as when the operation of the light source of the invention is desired to provide illumination and photocuring light power of the type and ranges for which it is capable of producing. It is preferred that the switch 188 be mounted in a remote location from the housing 18 and, for example, may be mounted upon the terminable end of arm yoke 10 located on the U-shaped member 12 or otherwise. The housing of the switch also includes a double-throw mutual switch 190 in which the arms are held together. A circuit breaker disconnect switch 192 is located at the post or input end of the arm and is included in each of the power lines through the switch members 190. In addition, a ground wire 194 is provided.

As a further safety precaution in operating the turntable 64, referring to FIG. 3, it will be seen that a stop 196 is fixed to the base 28 adjacent the window panel 42 and when the turntable is turned 90° in either direction relative to said stop, either the camming roller 164 engages the stop to prevent further rotation such as when the filter 126 is disposed adjacent the lamp 106 or a further abutment 198, see FIG. 3 adjacent the spring-actuated positioning ball check device 120, is fixed to the turntable 64 and abuts the stop member 196 on base 28 and prevents any further movement such as when the filter 130 has been disposed adjacent the reflector of lamp 106. Accordingly, it will be seen that the turntable 64 moves only through 180° comprising two excursions of 90° each.

From the foregoing, it will be seen that the present invention provides a compact and highly efficient dental operating light source by which at least three different types of illumination and one type of photocuring light power can be delivered in a dental operatory relative to dental targets. These types of illumination and photocure light power are normal white light free of color hue for general dental observation, intensified white light at a higher color temperature for shade matching and comparing function, no-cure illumination for use in observing light-curable plastic but without activating the same, and light-curing or photocuring light power for purposes of activating light-curable plastics. Because of the compact design, the structure occupies a relatively small space in a dental operatory as compared to three or four separate light sources respectively for purposes of providing the three types of illumination and one type of photocuring light power enumerated above. Because of circuitry of advanced design, the tungsten halogen lamp with a parabolic reflector is assured of reasonably long life under circumstances where the current to the lamp is constantly turned on and off, and all of the different optical functions are guarded against power line voltage fluctuations so as to deliver constant light output from the lamp. All of the various light beam-modifying structures are compactly housed within a space in which they are amply protected and columnation of the light beams directed from the front window panel are reasonably preserved. The housing or casing which, preferably, is adjustably mounted on the distal end of a supporting arm is adaptable to various types of mountings presently available for use in dental operatories. Two manually operable handles are provided which extend from the housing to allow for manual pivotal and swivelled positioning of the housing relative to a patient. Also, a safety means is provided for the photocure function.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

It is claimed:

1. A multi-functional dental operative light having at least two optical filters supported upon means movably adapted selectively to position one of said filters relative to a stationary light source having a parabolic reflector adapted to columnate light beams therefrom, beam splitting reflectors also mounted upon said means and positioned in the beam path from said light source and arranged to direct diverging light beams respectively to reflecting mirrors fixed to said means in spaced relationship and angled toward each other and operable to direct separate light beams in converging directions toward a dental target to be illuminated at a specified distance from said means by substantially preserving columnation of the light source in accordance with said selected optical filter, said filters of which at least two are included in the multi-functional light respectively are capable of producing white light beams substantially free of color for oral illumination, light beams in the yellow to orange range incapable of polymerizing visible light-curable material in an oral cavity, and light beams of reduced brightness and capable of effecting photocuring of a light-curable material.

2. The dental operative light source according to claim 1 in which the different optical characteristics of said filters are respectively adapted to produce white light beams substantially free of color having a wavelength range between 400 and 715 nm, said light beams to produce illumination in the yellow to red range having wavelengths between 400 and 500 nm removed from the beams but passing wavelengths greater than 500 nm, and the light beams to effect photocuring having the principal wavelengths in a range between 400 and 500 nm which reject most of the wavelengths greater than 500 nm.

3. The dental operative light source according to claim 2 in which said light source comprises a tungsten halogen lamp having a filament and a circuit from said lamp which is connectable to a power line source, said circuit also having a control switch and potentiometer adapted to vary the voltage to the filament of said lamp within ranges correspondingly to vary the light output and spectral wavelength distribution of the illumination emanating from said optical filters respectively to effect the aforementioned illumination for dental and/or medical purposes.

4. The dental operative light source according to claim 2 in which said light source is an arc type lamp and a circuit to said lamp which is connectable to a power line source and said circuit also having a control switch and potentiometer adapted to vary the power to said lamp within ranges correspondingly to vary the light output and spectral wavelength distribution of the illumination emanating from said optical filters respectively to effect the aforementioned illumination for dental and/or medical purposes.

5. A multi-function operating light source comprising, in combination, a series of optical filters mounted upon a turntable rotatable about a fixed axis in spaced relationship to each other relative to a stationary lamp having a parabolic reflector, said filters respectively being adapted selectively to produce; a pure white light relatively free from any color hue for illumination purposes; a noncuring light incapable of polymerizing light-curable resins when exposed to said light but permit observation; and a photocuring light of a light intensity and wavelength range capable of effecting polymerization of light-curable resins when said optical filters are disposed selectively adjacent said light; and control means in an electronic circuit to said lamp from a power line source operable to regulate voltage supply to the lamp according to the capacities of said optical filters to produce the desired illumination potentials afforded by said respective optical filters.

6. The operating light source according to claim 5 further including reflectors fixedly mounted relative to and spaced from opposite sides of said light source, and beam-splitting reflectors forward of said light source adapted to split the light beam from said source and direct the same respectively to said fixed reflectors, said reflectors being positioned angularly to direct said light beams in substantially columnated manner to a desired target.

7. The operating light source according to claim 6 further including a base having a front side and an opposite rear side and relative to which said turntable is rotatable and to which base said light source and reflectors are fixed relative to the rear side of said base, and a window fixed to the front side of said base and through which nearly columnated light beams emanating from said light source are projected.

8. The operating light source according to claim 6 in which said beam-splitting reflectors are mounted fixedly upon said turntable respectively adjacent said optical filter adapted to produce white light for desired illumination applications and said optical filter for producing nonpolymerizing illumination.

9. The operative light source according to claim 5 in which the color temperature of said lamp is approximately 3000° K. and said control means in circuit with said lamp is capable of adjusting the voltage to the lamp filament to provide a color temperature resulting from said optical filter by which white light is produced to between 4700° K. and 5100° K. to provide illumination suitable for visual observation of a desired target object.

10. The operative light source according to claim 5 in which the color temperature of said lamp is increased approximately to 3400° K. and said filter to produce pure white light is selected to raise the resulting color temperature to approximately 5500° K. and is adjustable and operable over a range between 5400° K. and 5900° K. for use in color-matching of different objects.

11. The operative light source according to claim 5 in which the optical filter to produce noncuring light is operable to remove light from the beam wavelength range between 400 and 500 nm from the light produced by said lamp, whereby the resulting noncuring light beams are in the yellow to red color range which is incapable of polymerizing visible light-curable resins when in the presence of such light beams.

12. The operative light source according to claim 5 in which the control means contains a circuit to said lamp which is adjustable to furnish an energizing voltage to said lamp which produces white light illumination having a color temperature within the range between 4700° K. and 5100° K. to provide normal illumination of a target, said control means also being operable to increase said color temperature to approximately 5500° K. suitable to permit color-matching of colored materials.

13. The operative light source according to claim 5 further including a manually engageable knob fixed to said turntable and projecting downward through a base and a housing therefor and operable to effect rotation of said turntable, and also including releasable position-maintaining means engageable by said turntable when each position thereof is reached relative to said base to maintain accurate alignment of said filters with said light source.

14. The multi-function operating light source according to claim 5 in which said photocuring light comprises a frustoconical primary light-condensing cone member fixed upon said turntable for movement therewith to and from operative positions in which one end of said member is adjacent said lamp, said turntable being rotatable upon a stationary base plate having front and rear edges and said lamp being fixed thereto adjacent said rear edge, a perpendicular front panel fixed to the front edge of said base plate and having an opening opposite the output end of said primary light-condensing cone member when said member is in operative position relative to said lamp, a supplemental light-condensing cone member adapted to be attached to the output end of said primary light-condensing cone member and extend through said opening in said front panel to provide desirable substantially columnated light from said lamp, and a closure selectively operable to be positioned across said opening when said supplemental light-condensing cone member is removed from said primary light-condensing cone member or removed from said opening when the supplemental cone member is attached to the primary cone member.

15. The multi-function operating light source according to claim 14 further including an electronic circuit attachable at one end to a power line source and connected to said lamp, said circuit further having a setable timer and switch connected therein, and said switch having an actuating member operable automatically to be engaged by said turntable when it is rotated to dispose the primary light-condensing cone member in operative position to open said switch and thereby break the power line circuit to said lamp and thus prevent a light beam from said lamp shining into a patient's eyes incident to mounting the supplemental light-condensing cone member upon the primary light-condensing cone member, and an additional switch operable to re-establish the circuit to deliver power to said lamp after the preset time of said setable timer has elapsed and said switch has disconnected the circuit to said lamp.

16. The multi-function operating light source according to claim 15 in which the switch of said setable timer is operated by a small synchronous electric motor having a cam thereon engageable with the movable switch member to open it.

17. A multi-function dental operating light source comprising, in combination, a base plate member having front and rear sides and adapted to be supported relative to the head of a patient to direct various kinds and amounts of illumination to perform desired dental practices, a carousel type turntable supported by said base plate member for rotation about an axis perpendicular thereto, a lamp having a parabolic reflector and supported fixedly upon said base plate adjacent the rear side thereof, a pair of spherical reflectors mounted fixedly upon the rear side of said base plate member and spaced from opposite sides of said lamp, a vertical transparent window positioned perpendicularly at the front side of said base plate, said turntable supporting in fixed spaced relationship to each other on an axis transverse to the axis of the light beam from said lamp a pair of optical filters movable selectively to positions in line with said light beam, one of said optical filters being a type which reshapes the optical spectrum of the light from said lamp to have a wavelength range between 400 and 715 nm for viewing a dental target on a patient, the other filter of said pair being of a type which reshapes the optical spectrum of light from said lamp to eliminate the wavelength range between 400 and 500 nm for viewing a dental target on a patient but incapable of curing visible light-curable materials, said optical filters respectively having a pair of beam-splitting reflectors mounted adjacent the inner surface of said optical filters and adapted to reflect light from said optical filters respectively to said spherical reflectors and from there through said vertical transparent window and toward a patient substantially in a columnated optical configuration, and said turntable also supporting between said pair of optical filters a primary light-condensing cone member having an optical filter at the light input end and a wavelength output in a range between 400 and 500 nm and including collimating means to effect a limited degree of beam divergence capable of curing visible light-curable dental plastic material, whereby a substantially universal dental light source instrument is provided which is capable of supplying illumination and photocuring power for substantially all normal needs of the same in the practice of dentistry.

18. The dental operating light source according to claim 17 further including cooling means for said lamp mounted upon said base plate adjacent said lamp comprising a heat absorbing filter adjacent the light beam-emanating end of said lamp.

19. The dental operating light source according to claim 18 in which said cooling means also comprises a fan driven by an electric motor, and means connecting said motor to said power line supply circuit and said lamp for operation of said motor which automatically operates when said lamp is illuminated or is not illuminated when in the photocure timer circuit operating mode.

20. The dental operating light source according to claim 17 in which said beam-splitting reflectors respectively associated with said pair of optical filters are positioned relative to said fixed spherical reflectors in a manner to project beams from said reflectors and whereby some of said beams cross each other at a predetermined distance forwardly of said transparent window and each projected beam is approximately parallel and together with said crossed beams jointly produce a column of illumination of limited width and height at a normal observation distance in a range between 24 and 37 inches forwardly of the window on said base plate.

21. The dental operating light source according to claim 17 further including an electronic circuit between the said lamp and a power line source and operable to maintain a constant predetermined voltage to said lamp regardless of inherent changes in the power line source voltage and said circuit including a manually-operated potentiometer connected to said electronic circuit and operable as said potentiometer is varied manually to change the voltage to said lamp, thereby to produce the required voltages to produce respective illumination intensities and spectral wavelength content by operation of only a single manual control member of said potentiometer.

22. The dental operating light source according to claim 17 in which a heat absorbing filter also is mounted in the light beam path from the reflector of said lamp, said heat absorbing filter also being operable to render the resulting illuminating beams relatively cool due to the elimination of infrared rays and thereby preventing heat rays from reaching said beam-modifying optical filters.

23. The dental operating light source according to claim 17 in which said light-condensing cone member comprises an elongated cone positioned between said pairs of beam-splitting reflectors, whereby there is no optical interference with the functioning of said reflectors and the assembly of said cone and filters is rendered compact.

24. The multi-functional dental operative light according to claim 1 further characterized by said reflecting mirrors being spherical.

25. The dental operative light source according to claim 1 in which said filters are circumferentially spaced around the axis of rotation of a turntable, respectively to present a selected filter in alignment with said light source to produce reflected beams of desired wavelengths toward said target.

* * * * *